(12) United States Patent
Hara et al.

(10) Patent No.: US 8,703,433 B2
(45) Date of Patent: Apr. 22, 2014

(54) MARKER FOR AMYOTROPHIC LATERAL SCLEROSIS, AND USE THEREOF

(75) Inventors: Hideaki Hara, Gifu (JP); Masamitsu Shimazawa, Gifu (JP); Hirotaka Tanaka, Gifu (JP)

(73) Assignee: Hideaki Hara, Gifu-Shi (JP)

( * ) Notice: Subject to any disclaimer, the term of this patent is extended or adjusted under 35 U.S.C. 154(b) by 0 days.

(21) Appl. No.: 13/880,062

(22) PCT Filed: Sep. 20, 2011

(86) PCT No.: PCT/JP2011/071311
§ 371 (c)(1),
(2), (4) Date: Apr. 18, 2013

(87) PCT Pub. No.: WO2012/053305
PCT Pub. Date: Apr. 26, 2012

(65) Prior Publication Data
US 2013/0210033 A1     Aug. 15, 2013

(30) Foreign Application Priority Data

Oct. 18, 2010   (JP) ................................ 2010-233210

(51) Int. Cl.
*G01N 33/53*   (2006.01)
*C07K 16/00*   (2006.01)

(52) U.S. Cl.
USPC .......................................... 435/7.1; 530/395

(58) Field of Classification Search
CPC combination set(s) only.
See application file for complete search history.

(56) References Cited

U.S. PATENT DOCUMENTS

| | | | |
|---|---|---|---|
| 2002/0168653 A1* | 11/2002 | Rameshwar | ...................... 435/6 |
| 2003/0064947 A1* | 4/2003 | Wang et al. | ...................... 514/44 |
| 2007/0298998 A1 | 12/2007 | Paige et al. | |
| 2009/0012928 A1 | 1/2009 | Lussier et al. | |
| 2010/0173340 A1* | 7/2010 | Adler et al. | ...................... 435/18 |
| 2011/0104739 A1 | 5/2011 | Bowser et al. | |

FOREIGN PATENT DOCUMENTS

| | | | | |
|---|---|---|---|---|
| EP | 1522857 | * | 3/2005 | ............. G01N 33/94 |
| JP | 2006-514620 A | | 5/2006 | |
| JP | 2007-528487 A | | 10/2007 | |
| JP | 2009-528059 A | | 8/2009 | |
| WO | WO/2008/133641 | * | 6/2008 | ........... G01N 33/574 |

OTHER PUBLICATIONS

Kimura et al., (The Japanese Pharmacological Society Kinki Bukai Program Yoshishu, Nov. 9, 2010, vol.118th, p. 34, Abstract A-11, partial translation provided).*
Qian et al, Molecular Oncology 2008;vol. 2, pp. 81-93.*
Q. Liao et al., "Serum proteome analysis for profiling protein markers associated with carcinogenesis and lymph node metastasis in nasopharyngeal carcinoma," Clin Exp Metastasis. Jun. 2008; 25, pp. 465-476.
R. Bowser et al., "Applying Proteomics to the Diagnosis and Treatment of ALS and Related Diseases," Muscle Nerve., Nov. 2009; 40(5), pp. 753-762.
C. Kolarcik et al., "Plasma and Cerebrospinal Fluid-Based Protein Biomarkers for Motor Neuron Disease," Mol Diagn Ther. 2006; 10(5), pp. 281-92.

* cited by examiner

*Primary Examiner* — Jacob Cheu
*Assistant Examiner* — Carmencita M Belei
(74) *Attorney, Agent, or Firm* — Edwards Wildman Palmer LLP; James E. Armstrong, IV

(57) ABSTRACT

An object is to provide a biomarker specific to amyotrophic lateral sclerosis and a use thereof. Provided are a marker for amyotrophic lateral sclerosis containing a transmembrane glycoprotein nmb, and a method for detecting amyotrophic lateral sclerosis, which utilizes the marker, and the like.

7 Claims, 9 Drawing Sheets

| Entrez Gene ID | Gene name | Log2Ratio (ALS/WT) |
| --- | --- | --- |
| 93695 | glycoprotein (transmembrane) nmb | 5.89 |
| 20303 | chemokine (C-C motif) ligand 4 | 5.86 |
| 21857 | tissue inhibitor of metalloproteinase 1 | 5.30 |
| 12642 | cholesterol 25-hydroxylase | 5.00 |
| 16956 | lipoprotein lipase | 4.95 |
| 56644 | C-type lectin domain family 7, member a | 4.84 |
| 22226 | urocortin | 4.83 |
| 20304 | chemokine (C-C motif) ligand 5 | 4.66 |
| 16854 | lectin, galactose binding, soluble 3 | 4.60 |
| 12971 | crystallin, mu | 4.58 |
| 11813 | apolipoprotein C-II | 4.57 |
| 57435 | plasma membrane associated protein, S3-12 | 4.55 |
| 109225 | membrane-spanning 4-domains, subfamily A, member 7 | 4.55 |
| 109225 | membrane-spanning 4-domains, subfamily A, member 7 | 4.47 |
| 80891 | Fc receptor-like S, scavenger receptor | 4.46 |
| 12045 | B-cell leukemia/lymphoma 2 related protein A1b | 4.38 |
| 15945 | chemokine (C-X-C motif) ligand 10 | 4.36 |
| 12514 | CD68 antigen | 4.34 |
| 235505 | CD109 antigen | 4.28 |
| 73690 | GLI pathogenesis-related 1 (glioma) | 4.27 |
| 12046 | B-cell leukemia/lymphoma 2 related protein A1c | 4.20 |
| 20296 | chemokine (C-C motif) ligand 2 | 4.19 |
| 12523 | CD84 antigen | 4.18 |
| 80891 | Fc receptor-like S, scavenger receptor | 4.14 |
| 20288 | macrophage scavenger receptor 1 | 4.05 |
| 23833 | CD52 antigen | 4.02 |
| 67742 | SAM domain, SH3 domain and nuclear localization signals, 1 | 4.01 |
| 12517 | CD72 antigen | 4.01 |
| 83433 | triggering receptor expressed on myeloid cells 2 | 4.00 |
| 11910 | activating transcription factor 3 | 3.97 |

Fig. 2

(a) Control

| Case | Age of death (years) | sex | PMI (h) | Cause of death |
|---|---|---|---|---|
| 1 | 70 | F | 3.8 | Brain-stem infarction |
| 2 | 64 | F | 2.0 | Multiple myositis |
| 3 | 70 | M | 2.0 | Multiple cerebral infarction |
| Mean ± SD | 68.0 ± 3.5 | | 2.6 ± 1.1 | |

(b) Sporadic ALS

| Case | Age of death (years) | sex | PMI (h) | duration of disease (month) |
|---|---|---|---|---|
| 1 | 80 | M | 2.7 | 72 |
| 2 | 49 | F | 2.5 | 40 |
| 3 | 57 | M | 2.5 | 9 |
| Mean ± SD | 62.0 ±16.1 | | 2.6 ± 0.1 | 40.3 ± 31.5 |

Fig. 6

| (a) Control | | | (b) Sporadic ALS | | |
|---|---|---|---|---|---|
| Case | Age (years) | Sex | Case | Age (years) | Sex |
| 1 | 25 | M | 1 | 67 | M |
| 2 | 29 | M | 2 | 69 | M |
| 3 | 27 | F | 3 | 79 | F |
| 4 | - | F | 4 | 70 | F |
| 5 | 28 | F | 5 | 53 | F |
| 6 | 33 | F | 6 | 80 | F |
| 7 | 67 | F | 7 | 74 | F |
| 8 | 60 | F | 8 | 63 | F |
| 9 | 74 | M | 9 | 63 | M |
| 10 | 67 | F | 10 | 46 | F |
| Mean ± SD | 45.5 ± 20.7 | - | Mean ± SD | 66.4 ± 10.1 | - |

Fig. 8

MARKER FOR AMYOTROPHIC LATERAL SCLEROSIS, AND USE THEREOF

SEQUENCE LISTING

The instant application contains a Sequence Listing which has been submitted in ASCII format via EFS-Web Apr. 18, 2013, is named U.S. Ser. No. 13/880,062 and is 18,241 bytes in size.

TECHNICAL FIELD

The present invention relates to a marker for amyotrophic lateral sclerosis useful for detection of amyotrophic lateral sclerosis. Specifically, the invention relates to a biomarker usable for determination of the possibility of the onset of amyotrophic lateral sclerosis and a method for detecting amyotrophic lateral sclerosis, which utilizes the biomarker. The present application claims the priority based on Japanese Patent Application No. 2010-233210 filed on Oct. 18, 2010, and the whole content of the patent application is incorporated herein by reference.

BACKGROUND ART

Amyotrophic lateral sclerosis (ALS) is a chronic progressive degenerative disease, which damages almost selectively the upper and lower motor neurons. The predominant symptom of ALS is loss of muscle strength due to degeneration of the motor neuron, but the sensory neuron is normal and a patient loses motor control but feels pain, and thus, ALS is a very cruel disease. A glutamate antagonist, riluzole has been solely used as a therapeutic agent, but a satisfactory effect cannot be attained. ALS is an incurable nervous disease, for which an effective therapeutic method cannot be found even now regardless of vigorous research activities for a long period of time, and urgent clarification of the mechanism of the onset and development of a therapeutic agent are required.

PRIOR ART DOCUMENTS

Patent Documents

Patent Document 1: Japanese Unexamined Patent Application Publication (Translation of PCT Application Publication) No. 2006-514620
Patent Document 2: Japanese Unexamined Patent Application Publication (Translation of PCT Application Publication) No. 2009-528059
Patent Document 3: Japanese Unexamined Patent Application Publication (Translation of PCT Application Publication) No. 2007-528487

Non-Patent Documents

Non-patent Document 1: Serum proteome analysis for profiling protein markers associated with carcinogenesis and lymph node metastasis in nasopharyngeal carcinoma., Clin Exp Metastasis., 2008.
Non-patent Document 2: APPLYING PROTEOMICS TO THE DIAGNOSIS AND TREATMENT OF ALS AND RELATED DISEASES., Muscle Nerve., 2009.
Non-patent Document 3: Plasma and Cerebrospinal Fluid-Based Protein Biomarkers for Motor Neuron Disease., Mol Diag Ther., 2006.

SUMMARY OF THE INVENTION

Problems to be Solved by the Invention

Many ALS pathologic related molecules have been identified in researches for a long time (for example, see Patent Documents 1 to 3, Non-patent Documents 1 to 3); however, a cause of ALS is still indefinite. With current techniques, needless to say, the onset of ALS (or the possibility of the onset) cannot be figured out in the early stage, and even diagnosis of ALS is not easy. Therapeutic intervention is delayed since an objective indication useful for diagnosis of ALS does not exist, and as a result, quite a lot cases become intractable.

Thus, an object of the present invention is to provide a biomarker specific to ALS and a use thereof, that is, a technique useful for detection of ALS, in order to enable diagnosis of ALS in the early stage and diagnosis of ALS with high credibility. Specifically, an object of the present invention is to provide a biomarker useful for detection of ALS, a detection method which utilizes the biomarker, and a detection reagent which is used in the detection method.

Means for Solving Problem

The present inventors carried on studies using an ALS model mouse in order to find out a biomarker specific to ALS. As a result of a detail analysis by a DNA microarray method, significant increase of a transmembrane glycoprotein nmb (glycoprotein (transmembrane) nmb; GPNMB) mRNA was observed in the spinal cord of the ALS model mouse. Thus, as a result of being studied focusing on the molecule, it was suggested that GPNMB relates to formation of pathologic condition of ALS such that GPNMB localizes in a motor nerve cell and an astroglial cell. In addition, increase of an expression amount of GPNMB was observed in the spinal cord of an ALS model mouse as compared to an expression amount before the onset; at the same time, it was revealed that an expression amount of GPNMB increased accompanied by the development of pathologic conditions. On the other hand, as a result of progressing further study in use of a clinical sample of an ALS patient, aggregation and deposition of GPNMB was observed in the anterior horn of the spinal cord of the ALS patient, and at the same time, significant increase of GPNMB was observed in the serum of the ALS patient. That is, it was shown that GPNMB is clinically extremely useful as a biomarker of ALS. The present inventions described below are mainly based on the above-described achievements.

[1] A marker for amyotrophic lateral sclerosis, containing a transmembrane glycoprotein nmb.

[2] A method for detecting amyotrophic lateral sclerosis, wherein a level of a transmembrane glycoprotein nmb in a specimen is used as an indication.

[3] The method for detecting amyotrophic lateral sclerosis according to [2], including the following steps (1) to (3):
 (1) a step of preparing a specimen derived from a subject;
 (2) a step of detecting a transmembrane glycoprotein nmb in the specimen; and
 (3) a step of determining present or future possibility of the onset of amyotrophic lateral sclerosis based on the detected results.

[4] The method for detecting amyotrophic lateral sclerosis according to [3], wherein the determination in the step (3) is performed in accordance with the criterion in which the possibility of the onset is high as a detected value is high, or the in which the possibility of the onset is high as detection can be performed.

[5] The method for detecting amyotrophic lateral sclerosis according to [3] or [4], wherein the determination of the step (3) is performed based on comparison between a detected value obtained in the step (2) and a detected value of a control specimen.

[6] The method for detecting amyotrophic lateral sclerosis according to [3] or [4], wherein the determination of the step (3) is performed based on comparison between a detected value obtained in the step (2) and a detected value of a specimen obtained from the same subject in the past.

[7] The method for detecting amyotrophic lateral sclerosis according to any one of [2] to [6], wherein the specimen is blood, plasma, serum, spinal cord, or cerebrospinal fluid.

[8] A reagent for detecting amyotrophic lateral sclerosis, containing a substance showing a specific binding activity to the marker for amyotrophic lateral sclerosis according to [1].

[9] The reagent for detecting amyotrophic lateral sclerosis according to [8], wherein the substance is an antibody.

[10] A kit for detecting amyotrophic lateral sclerosis, containing the reagent for detecting amyotrophic lateral sclerosis according to [8] or [9].

BRIEF DESCRIPTION OF THE DRAWINGS

FIG. 2 is a table showing top 30 genes having twice or more expression between SOD1$^{G93A}$ mice and WT mice and significant (p<0.05) increased expression.

FIG. 6 shows a table summarizing backgrounds of 6 examples of subjects whose spinal cord tissues were extracted. The data of ages and post mortem intervals (PMI) are expressed as means±standard deviation. M: male, F: female.

FIG. 8 is a table summarizing backgrounds of 20 examples of subjects whose serum samples were obtained. The data of ages are expressed as mean±standard deviation.

MODE FOR CARRYING OUT THE INVENTION

Figure 1:
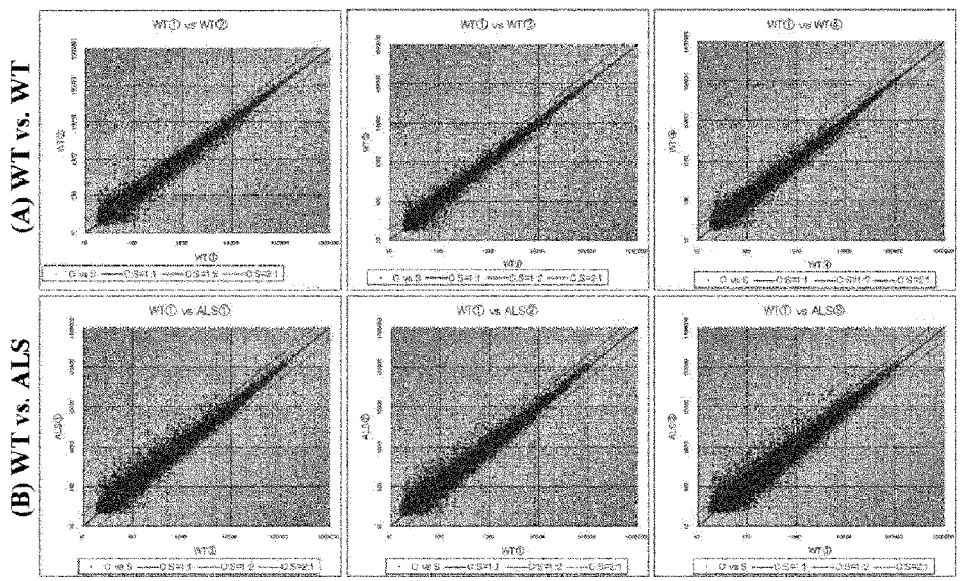
FIG. 1 shows a scatchard plot, which was produced according to results of DNA microarray using spinal cords of 14-week old SOD1$^{G93A}$ and wild type mice (WT). (A) shows a difference of gene expression between WT mice, and (B) shows a difference of gene expression between WT and SOD1$^{G93A}$ mice, respectively. The upper line and the lower line show 2-fold increase and decrease of expressed genes, respectively.

First Aspect of the Present Invention: Biomarker of Amyotrophic Lateral Sclerosis (ALS)

The first aspect of the present invention relates to a biomarker of ALS (hereinafter also referred to as "the biomarker of the invention"). The biomarker of the invention is a useful indication for evaluating the present or future possibility of the onset of ALS. For "the present possibility of the onset", whether ALS is developed or not or probability of the onset at the time of detection is expressed. On the other hand, "the future possibility of the onset" indicates the possibility (risk) of developing ALS in future.

As an achievement of studies by the present inventors, the biomarker of the invention consists of a molecule, "a transmembrane glycoprotein nmb (glycoprotein (transmembrane) nmb)", which has been recognized to have a mutual relation with ALS. The molecule will be expressed using its genetic symbol "GPNMB" in the description below according to the custom.

GPNMB is a transmembrane glycoprotein showing homology to melanocyte specific protein Pmel17. Two transcription variants for GPNMB, that is, an isoform a made of 572 amino acids and an isoform b made of 560 amino acids exist. It has been reported that GPNMB is highly expressed in specific kinds of cancers (such as melanoma, glioma, and breast cancer), and GPNMB is focused as a target of an antibody therapy against melanoma and breast cancer. Note that the amino acid sequence of the isoform a of GPNMB and the nucleotide sequence coding for the amino acid sequence are set forth as SEQ ID NO: 1 (ACCESSION of NCBI: NP_001005340, DEFINITION: transmembrane glycoprotein NMB isoform a precursor [Homo sapiens].) and SEQ ID NO: 2 (ACCESSION of NCBI: NM_001005340, DEFINITION: Homo sapiens glycoprotein (transmembrane) nmb (GPNMB), transcript variant 1, mRNA.) in the sequence listing, respectively. In the same manner, the amino acid sequence of isoform b of GPNMB and a nucleotide sequence coding for the amino acid sequence are set forth as SEQ ID NO: 3 (ACCESSION of NCBI: NP_002501, DEFINITION: transmembrane glycoprotein NMB isoform b precursor [Homo sapiens].) and SEQ ID NO: 4 (ACCESSION of NCBI: NM_002510, DEFINITION: Homo sapiens glycoprotein (transmembrane) nmb (GPNMB), transcript variant 2, mRNA.).

Second Aspect of the Present Invention: ALS Detection Method

The second aspect of the present invention relates to a use of the above-described biomarker of the invention, and a method for detecting the present or future possibility of the onset of ALS (hereinafter also referred to as "the detection method of the invention"). The detection method of the present invention is useful as a means for determining whether ALS is currently developed or not, or as a means for determining whether ALS will be developed in future or not. That is, the detection method of the present invention provides useful information for diagnosing ALS. The detection method of the present invention enables to simply and objectively determine the possibility of the onset of ALS.

In the detection method of the present invention, a level of the biomarker of the present invention in a specimen derived from a subject is used as an indication. The "level" herein typically means "amount" or "concentration". However, the term "level" is also used in the case of expressing whether a molecule to be detected can be detected or not (that is, presence or absence of apparent existence), according to the custom and technical common knowledge.

The following steps are carried out in the detection method of the present invention:

(1) a step of preparing a specimen derived from a subject;
(2) a step of detecting a transmembrane glycoprotein nmb in the specimen; and
(3) a step of determining the present or future possibility of the onset of amyotrophic lateral sclerosis based on the detected results.

A subject-derived specimen is prepared in the step (1). The blood, plasma, serum, spinal cord, and cerebrospinal cord fluid of the subject can be used as the specimen. The subject is not particularly limited. That is, the present invention can be broadly applied to a subject necessary for determination of the present or future possibility of the onset of ALS (that is, presence or absence of the possibility of developing ALS, a degree of the possibility of developing ALS, and a degree of the possibility of developing ALS in future). For example, when the present invention is applied to a patient who is diagnosed to be ALS by doctor's questions, advisability of the diagnosis can be determined based on an objective indication that is an expression level. That is, information that aids or supports conventional diagnosis can be obtained according to the detection method of the present invention. Such information is beneficial to determination of a more suitable therapeutic strategy, and promotes improvement in therapeutic effect and improvement in patient's QOL (Quality of Life). On the other hand, the present invention is utilized for monitoring diseased conditions and can attempt prevention of intractability, severity, recurrence, and the like.

A person who is assumed to have a high risk of ALS affection from the family background (high risk person) is also a suitable subject. To apply the present invention before appearing symptoms of ALS to such a subject enables inhibition or retardation of the onset, or therapeutic intervention in the early stage. The present invention is also useful to identify a person having a high risk of ALS affection. Such identification enables lowering of the possibility of the onset (the possibility of disease affection) due to, for example, preventive measures and improvement of lifestyles. A person who is incapable of being determined to be ALS or not or is hardly determined to be ALS or not by conventional diagnosis, such as a person with no certain symptom, is also a suitable subject of the present invention. Note that the present invention may also be carried out as one item of a medical examination.

The biomarker of the present invention in a specimen is detected in the step (2). Accurate quantitative determination of the level of the biomarker is not essential. That is, the level of the biomarker may be detected to a degree in which the possibility of the onset of ALS can be determined in the following step (3). For example, the detection can also be carried out so as to be able to determine whether the level of the biomarker in a specimen exceeds the predetermined standard value or not.

The detection method of the biomarker is not particularly limited. However, an immunologic technique is preferably used. The immunologic technique enables the rapid detection with high sensitivity. Furthermore, the immunologic technique can be carried out in an easy and simple manner. In the measurement by the immunologic technique, a substance having a specific binding activity with respect to the biomaker is used. As the substance, an antibody is generally used. However, the substance is not necessarily limited to the antibody, and any substances can be used as long as they have a specific binding activity with respect to the biomarker and the binding amount can be measured. Other than antibodies commercially available, newly prepared antibodies by an immunologic technique, a phage display method or a ribosome display method can be used.

Examples of the measurement method include a latex agglutination method, a fluorescence immunoassay (FIA) method, an enzyme immunoassay (EIA) method, a radioimmunoassay (RIA) method, and a Western blotting method. Preferable measurement method can be a FIA method and an EIA method (including an ELISA method). With these methods, detection can be carried out with high sensitivity, rapidly and in a simple and easy manner. In the FIA method, a fluorescent labeled antibody is used, and an antigen-antibody complex (an immune complex) is detected by using fluorescence as a signal. In the EIA method, an enzyme-labeled antibody is used, and an immune complex is detected by using coloring and light emission based on the enzyme reaction as a signal.

The ELISA method has many advantages, for example, detection sensitivity is high, specificity is high, quantitativity is high, an operation is simple, and multiple specimens can be handled simultaneously. One example of a specific operation in which the ELISA method is used is described hereinafter. Firstly, an anti-biomarker antibody is immobilized to an insoluble support. Specifically, for example, the surface of a microplate is sensitized (coated) with an anti-biomarker monoclonal antibody. A specimen is brought into contact with the thus solid-phased antibody. As a result of this operation, when an antigen (protein molecule, namely the biomarker) against the solid-phased anti-biomarker antibody is present in the specimen, an immune complex is formed. Nonspecific binding components are removed by washing, followed by adding an antibody to which an enzyme is bound so as to label the immune complex. Then, the substrate of the enzyme is reacted to develop color. Thus, the immune complex is detected using an amount of color development as an indicator. Since the detail of the ELISA method is described in many text books or papers, when experiment procedures or experiment conditions of each method are set, such books or papers can be referred to. Note here that not only noncompetitive methods but also competitive methods (methods in which an antigen is added together with a specimen so as to allow them to compete with each other) may be used. A method of directly detecting the biomarker in a specimen with a labeled antibody may be employed or a sandwich method may be employed. In the sandwich method, two types of antibodies (a capturing antibody and a detecting antibody) whose epitopes are different from each other are used.

A means capable of simultaneously detecting a large number of specimens such as a protein array and a protein chip may be used. For example, an antibody specific to a target biomarker is used for a probe.

The present or future possibility of the onset of ALS is determined based on detection results in the step (3). In order to enable precise determination, it is preferred to carry out the determination after the detected value obtained in the step (2) is compared to a detected value of a control specimen (control). The possibility of the onset may be determined qualitatively or quantitatively. Note here that, as is apparent from the determination criteria, the determination herein can be carried out automatically/mechanically without depending upon the judgment by persons having special technical knowledge, for example, medical doctors or laboratory technicians.

In the present invention, typically, the criterion in which "the possibility of the onset is high as a detected value of the biomarker is high", or the criterion in which "the possibility of the onset is high as the biomarker can be detected" is employed. Needless to say, the former criterion, that is, the criterion in which "the possibility of onset is high as a detected value of the biomarker is high" is used synonymously with the criterion in which "the possibility of the onset is low as a detected value of the biomarker is low" (the same applies to the latter criterion). Examples of the qualitative determination and quantitative determination are shown below.

Example 1 of Qualitative Determination

When a detected value (level in specimen) is higher than the reference value, it is determined that the "possibility of the onset is high." When a detected value (level in specimen) is lower than the reference value, it is determined that the "possibility of the onset is low."

Example 2 of Qualitative Determination

When the biomarker is detected (the reactivity is observed), it is determined that the "possibility of the onset is high." When the biomarker is not detected, it is determined that the "possibility of the onset is low."

Example of Quantitative Determination

As shown below, the possibility of the onset (%) is previously set for each range of the detected values, and the possibility of the onset (%) is determined from the detected value.
Detected values a-b: possibility of the onset is not more than 10%
Detected values b-c: possibility of the onset is 10% to 30%
Detected values c-d: possibility of the onset is 30% to 50%
Detected values d-e: possibility of the onset is 50% to 70%
Detected values e-f: possibility of the onset is 70% to 90%

The biomarker of the present invention could be a preferable sole determination indicator for ALS. However, another useful indicator for detection of ALS may also be used for determination of the possibility of the onset of ALS. That is, using the biomarker of the present invention and another indicator in combination, the possibility of the onset of ALS may be determined. Generally, diagnosis (detection) sensitivity and diagnosis (detection) specificity are different due to kinds and numbers of indicators to be combined. Therefore, it is desired to select the most appropriate combination of indicators according to a purpose. For example, a combination with high diagnosis sensitivity is suitable for detection by screening. In contrast, a combination with high diagnosis specificity is suitable for detection necessary for determination with high credibility (for example, secondary examination and tertiary examination). By combining determination methods having different balance between diagnosis sensitivity and diagnosis specificity, improvements in efficiency, accuracy and credibility can be attempted. For example, after focusing a positive subject using a combination of indicators providing high diagnosis sensitivity (primary examination, screening examination), final determination is made using a combination of indicators giving high diagnosis specificity (secondary examination). Determination with three or more steps can also be carried out, not limited to such a two-step determination.

Both of the number of determination sections and a level of a biomarker and determination results, which are associated with the determination sections, can be arbitrarily set through a preliminary experiment, or the like without limitation to the above-described examples. For example, "a threshold value" in the case of determining high and low possibilities of the onset assuming a certain threshold value as a boundary and "a range of a level of a biomarker" associated with a section relating to high and low possibilities of the onset can be determined by statistic analysis using a large number of specimens. In the case of making an analysis in use of a statistic analysis, setting a high risk group and a low risk group is generally effective. For example, a group of ALS patients or a group of persons who have many ALS patients in their family lines falls into the high risk group, and for example, a group of healthy subjects and a group of persons who have no ALS patient in their family lines falls into the low risk group.

In one embodiment of the present invention, for an identical subject, a level of a biomarker, which was measured at a certain time, and a level of a biomarker, which was measured in the past, are compared and presence or absence of increase and decrease of a level of a biomarker and/or a degree of increase and decrease is examined. Data relating to change in an expression level of a biomarker, which was obtained as a result, becomes useful information for monitoring the possibility of the onset of ALS, grasping therapeutic effects, or prognostic presumption. Concretely, for example, such determination that the possibility of the onset becomes high between the previous detection and the detection in this time or there is no variation can be made based on variation of a level of a biomarker as a ground. When such an evaluation is carried out in parallel to a therapy for ALS, needless to say, a therapeutic effect can be confirmed, and symptom of recurrence of ALS can be figured out. Accordingly, a more appropriate therapeutic measure can be determined. The present invention can thus largely contribute to maximization of therapeutic effects and improvement in QOL (quality of life) of a patient.

Third Aspect of the Present Invention: Reagent and Kit for Examination of the Possibility of the Onset of ALS The present invention further provides a reagent and a kit for examination of the possibility of the onset of ALS. The reagent of the present invention includes a substance (hereinafter, referred to as "binding molecule") which shows a specific binding activity to the biomarker of the present invention. Examples of the binding molecule include an antibody which specifically recognizes the biomarker, a nucleic-acid aptamer and peptide aptamer. Kinds or origins of the binding molecule are not particularly limited as long as it has a specific binding activity with respect to the biomarker. In the case of antibodies, a polyclonal antibody, an oligoclonal antibody (a mixture of several to several tens of kinds of antibodies), and a monoclonal antibody may be employed. As the polyclonal antibody or the oligoclonal antibody, in addition to an antiserum-derived IgG fraction obtained by immunizing animals, an affinity purified antibody by antigen can be used. The antibody may be antibody fragments such as Fab, Fab', F(ab')$_2$, scFv, dsFv antibodies.

The binding molecule can be prepared by a conventional method. Commercially available binding molecules can be used. For example, the antibody can be prepared by using an immunologic technique, a phage display technique, a ribosome display method, and the like. The preparation of polyclonal antibody by the immunologic technique can be carried out by the following procedure. An antigen (the biomarker or a part thereof) is prepared, and this is used to immunize an animal such as a mouse, a rat or a rabbit. By purifying the living body sample, an antigen can be obtained. A recombinant antigen can be also used. The recombinant antigen can be prepared by introducing a gene encoding the biomarker (a part of the gene may be used) into a suitable host by using a vector to obtain a recombinant cell, and expressing the gene in the obtained recombinant in the cell.

In order to strengthen the immune elicitation, an antigen to which a carrier protein is bonded may be used. As the carrier protein, KLH (Keyhole Limpet Hemocyanin), BSA (Bovine Serum Albumin), OVA (Ovalbumin), and the like, are used. For bonding of the carrier protein, a carbodiimide method, a glutaraldehyde method, a diazo condensation method, a MBS (maleimidobenzoyloxy succinimide) method, and the like, can be used. On the other hand, it is possible to use an antigen in which the biomarker (or a part thereof) is allowed to be expressed as a fusion protein with GST, β galactosidase, maltose binding protein, or histidine (His) tag, and the like. Such a fusion protein can be purified by a general method in a simple and easy manner.

Immunization is repeated if necessary. At a time when an antibody value is sufficiently increased, blood is collected. The collected blood is subjected to centrifugation so as to obtain serum. The obtained anti-serum is subjected to affinity purification to give a polyclonal antibody.

On the other hand, the monoclonal antibody can be prepared by the following procedure. Firstly, immunization is carried out by the same procedure as mentioned above. Immunization is repeated if necessary. At the time when an antibody value is sufficiently increased, an antibody producing cell is extracted from an immunized animal. Next, the obtained antibody producing cell and myeloma cell are fused so as to obtain hybridoma. Subsequently, this hybridoma is made to be monoclonal. Clones capable of producing an antibody having high specificity with respect to the objective protein are selected. By purifying a culture solution of the selected clone, the objective antibody can be obtained. On the other hand, the hybridoma is allowed to proliferate to the predetermined number or more. Then, the proliferated hybridoma are transplanted into the abdominal cavity of an animal (for example, a mouse) and allowed to proliferate in the abdominal dropsy. By purifying the abdominal dropsy, the objective antibody can be obtained. For purification of the above-mentioned culture solution or purification of the abdominal dropsy, affinity chromatography using protein G, protein A, and the like, can be suitably used. Furthermore, affinity chromatography in which the antigen is immobilized to a solid phase can be used. Furthermore, methods such as ion exchange chromatography, gel filtration chromatography, ammonium sulfate fractionation, and centrifugation can be also used. These methods may be used singly or may be used in combination thereof.

Various modifications can be made to the obtained antibody on the condition that specific connectivity is maintained. Such a modified antibody may be included in the reagent of the present invention.

When a labeled antibody is used as the binding molecule, a binding amount of the antibody can be directly detected by using a labeling amount as an indicator. Therefore, a simpler and easier examination method can be established. However, there are problems that it is necessary to prepare an antibody to which a labeling substance is attached, and furthermore, the detecting sensitivity is generally lowered. Then, it is preferable to use indirect detection methods such as a method using a secondary antibody to which a labeling substance is attached and a method using a secondary antibody and a polymer to which a labeling substance is bound. The secondary antibody herein denotes an antibody having a specific binding activity to the anti-biomarker antibody. For example, when the anti-biomarker antibody is prepared as a rabbit antibody, an anti-rabbit IgG antibody can be used as a secondary antibody. Labeling secondary antibodies that can be used in various species such as rabbit, goat and mouse are commercially available (for example, products available from Funakoshi Corporation, COSMO BIO Co., Ltd.), and appropriate antibodies can be selected and used according to the reagent of the present invention.

Examples of the labeling substances include enzymes such as peroxidase, micro-peroxidase, horseradish peroxidase (HRP), alkaline phosphatase, β-D-galactosidase, glucose oxidase, and glucose-6-phosphate dehydrogenase; fluorescence substances such as fluorescein isothiocyanate (FITC), tetramethylrhodamine isothiocyanate (TRITC), and europium; chemiluminescence substances such as luminol, isoluminol and acridinium derivative; coenzymes such as NAD; biotin; as well as radioactive substances such as $^{131}$I and $^{125}$I.

In one embodiment, the reagent of the present invention is immobilized to a solid phase in accordance with the use. Insoluble supports to be used for immobilization into a solid phase are not particularly limited. For example, an insoluble support made of a substance insoluble in water, for example, resin such as polystyrene resin, polycarbonate resin, silicon resin, and nylon resin, glass, and the like can be used. An antibody can be supported to an insoluble support by physical adsorption or chemical adsorption.

The kit of the present invention includes the reagent of the present invention as a main component. The kit may include other reagents (buffer solution, blocking reagent, substrate for enzyme, coloring reagent, and the like) used for carrying out a examination method and/or a device or an instrument (a container, a reactor, a fluorescence reader, and the like). Furthermore, it is preferable that the kit includes the biomarker molecule or a fragment thereof as a standard sample. In general, an instruction manual is attached to the kit of the present invention.

EXAMPLES

The following experiment was carried out in an attempt to identify an ALS related molecule.
1. Materials and Methods
(1) Materials for Experiment Chemicals and reagents used in the experiment are as follows: Paraformaldehyde, sucrose, potassium chloride, ethanol, chloroform, methanol and a rabbit anti-ionized calcium-binding adaptor molecule 1 (Iba1) polyclonal antibody were purchased from Wako Pure Chemical Industries, Ltd. (Osaka, Japan), sodium hydrogen phosphate 12-water and sodium dihydrogen phosphate dehydrate were purchased from NACALAI TESQUE, INC. (Kyoto, Japan), xylene and sodium chloride were purchased from KISHIDA CHEMICAL Co., Ltd. (Osaka, Japan), Nembutal was purchased from Dainippon Sumitomo Pharma Co., Ltd. (Osaka, Japan), RNAlater-ICE was purchased from Life Technologies Japan Ltd. (Tokyo, Japan), normal goat serum, normal horse serum, a Vectastain elite Avidin Biotinylated Enzyme complex (ABC) kit, M.O.M. immunodetection kit and diaminobenzidine (DAB) peroxidase substrate kit were purchased from Vector Laboratories (Burlingame, USA), an O.C.T. compound was purchased from SAKURA SEMI Co., Ltd. (Tokyo, Japan), Can Get Signal (registered trademark) immunostain solution A was purchased from TOYOBO CO., LTD. (Osaka, Japan), a mouse anti-GPNMB polyclonal antibody was purchased from Santa Cruz Biotechnology (Santa Cruz, USA), a mouse anti-NeuN monoclonal antibody and a mouse anti-glial fibrillary acidic protein (GFAP) monoclonal antibody were purchased from Millipore (Bedford, USA), a mouse anti-CD11b monoclonal antibody was purchased from BMA Biomedicals (Augst, Switzerland), an Alexa 488 binding donkey anti-goat IgG antibody, Alexa 546 binding donkey anti-rabbit IgG antibody, Alexa 488 binding rabbit anti-mouse IgG antibody, Alexa 546 binding rabbit anti-goat IgG antibody and Hoechst 33342 were purchased from Invitrogen Corporation (Tokyo, Japan), fluoromount was purchased from Diagnostic BioSystems (Pleasanton, USA), an EUKITT reagent was purchased from O. Kindler (Freiburg, Germany), and Human Osteoactivin/GPNMB DuoSet was purchased from R & D Systems (Minneapolis, USA), respectively.

(2) Experimental Animals

An SOD1$^{G93A}$ mouse and a wild-type (WT) mouse [B6SJL-Tg (SOD1-G93A) 1 Gur/J] were purchased from Jackson Laboratory (Bar Harbor, USA). An SOD1$^{G93A}$ (+/−) mouse born through crossing a male SOD1$^{G93A}$ mouse and a female WT mouse was used in the experiment. The mouse was bred with a solid feed (CE-2, CLEA Japan, Inc., Tokyo, Japan) under free water supply using a plastic cage (breadth 24.5×width 17.5×height 12.5 cm). For carrying out the experiment, an animal experiment application for approval was filed to and approved by the steering committee of animal facility of Gifu Pharmaceutical University.

(3) DNA Microarray 14-week old male SOD1$^{G93A}$ mouse and a WT mouse were intraperitoneally administered with 20 mg/kg of nembutal to be deeply anesthetized, and physiological saline water (pH 7.4) was injected to the left ventricles and perfused for 2 minutes to thus isolate the spinal cords. The isolated tissues were contained in a cooled microtube and rapidly frozen. The samples were preserved at −80° C. until RNA extraction. The samples were infiltrated by RNAlater-ICE, and RNA extraction and analysis were performed in DNA Chip Research Inc. (Kanagawa, Japan).

(4) Real Time PCR

Real time PCR was carried out and measured by Thermal Cider Dice (registered trademark) Real Time System TP800 (TAKARA BIO INC.) using SYBR (registered trademark) Premix Ex Taq™II (TAKARA BIO INC.). Sense: 5'-TCTGAACCGAGCCCTGACATC-3' (SEQ ID NO: 5) and anti-sense: 5'-AGCAGTAGCGGCCATGTGAAG-3' (SEQ ID NO: 6) were used for primers of GPNMB. Sense: 5'-TGTGTCCGTCGTGGATCTGA-3' (SEQ ID NO: 7) and anti-sense: 5'-TTGCTGTTGAAGTCGCAGGAG-3' (SEQ ID NO: 8) were used for primers of glyceraldehyde-3-phosphate dehydrogenase (GAPDH). In the PCR reaction, denaturation was carried out at 95° C. for 5 seconds, and annealing and an extension reaction were carried out at 60° C. for 30 seconds. This reaction was assumed to be 1 cycle and 45 cycles were repeated. Reactions at 95° C. for 15 seconds, 60° C. for 30 seconds, and 95° C. for 15 seconds were carried out, a dissociation curve was drawn and the purity of the generated product was confirmed.

(5) Human Spinal Cord Tissue Sample

The examination was carried out after deliberation and approval of the ethical committee in Niigata University in accordance with the declaration of Helsinki. Furthermore, informed consents were executed to all subjects and name seals to consent forms for participation to the experiment were obtained. The subjects are 3 examples of sporadic ALS patients and 3 examples of nonneurogenic disease patients. Ages, sexes, post mortem intervals and durations of the disorder were shown in FIG. 6. All examinations using human spinal cord samples were carried out in the School of Medicine, Niigata University. Cervical spinal cord (C7), thoracic spinal cord (T8) and lumbar spinal cord (L8) were respectively embedded with paraffin to prepare 4 μm-cut pieces.

(6) Mouse Spinal Cord Tissue Sample 6-week old (before the onset), 10-week old (before the onset), 14-week old (after the onset) and 18 to 20-week old (end stage of pathologic condition) male SOD1$^{G93A}$ mice and WT mice were intraperitoneally administered with 20 mg/kg of nembutal to be deeply anesthetized, and a 4% paraformaldehyde-containing 0.1 M phosphoric acid buffer (PB; pH 7.4) was injected into the left ventricles for perfusion fix (perfusion pressure 130 cm H$_2$O). Spinal cords were taken out after 10 minutes, and stood still (4° C.) overnight in the same solution. Then, the spinal cords were stood still (4° C.) in a 25% sucrose-containing 0.1 M PB (pH 7.4) solution for 24 hours. Then, the spinal cords were embedded with O.C.T. compounds and rapidly frozen with liquid nitrogen and preserved at −80° C. until being thinly sliced. For thinly slicing, 14 μm-thick cut pieces were prepared at −20° C. using a cryostat (CM1850, Leica, Tokyo, Japan), and put on a slide glass coated with MAS (Matsunami Glass Ind., Ltd., Osaka, Japan) to be preserved at −80° C.

(7) Histological Study

The frozen cut pieces were taken out from −80° C. and left at −20° C. for 1 hour, then dried at room temperature for 10 minutes, and immersed into PBS to wash the O.C.T. compound. The paraffin cut pieces were immersed into xylene to wash paraffin. Then, the cut pieces were immersed into a solution having a decreased alcoholic concentration in stages and permeated with distilled water. Then, the circumferences of the cut pieces were enclosed with super PAP pen (ZYMED, San Francisco, USA) in order to prevent outflow of the reaction solution. The cut pieces were reacted with a 0.3% H$_2$O$_2$-containing methanol for 30 minutes, and then blocked with 10% normal horse serum for 2 hours. After blocking, the cut pieces were reacted with a goat anti-GPNMB polyclonal antibody (×50) diluted with Can Get Signal immunostain solution A at 4° C. overnight. Then, the cut pieces were reacted with a biotinylated anti-goat IgG antibody (×1,000) for 2 hours, and stained using a Vectastain Elite ABC kit and a DAB peroxidase substrate kit. After staining, the cut pieces were washed twice with distilled water for 2 minutes and immersed into 70% ethanol, 95% ethanol, 99% ethanol, and anhydrous ethanol in this order for 3 minutes each to be dehydrated. The dehydrated cut pieces were immersed into xylene twice for 5 minutes to be penetrated, and then encapsulated into a cover glass using an EUKITT reagent. A control obtained by removing a primary antibody was prepared for a negative control, and specificity of the primary antibody was studied. The cut pieces were observed under a microscope (BX50, Olympus Corporation, Tokyo, Japan) and recorded using a digital camera (COOLPIX 4500, NIKON CORPORATION, Tokyo, Japan).

(8) Immunofluorescence Double Staining

Outflow of a reaction solution was prevented from a mouse tissue cut piece in accordance with the method described in (7) and the mouse tissue cut piece was blocked with an M.O.M. immunodetection kit or a 10% normal horse serum for 2 hours. After blocking, the cut piece was reacted using primary antibodies at 4° C. overnight. Then, the cut piece was reacted with secondary antibodies for 2 hours. After staining, the cut piece was reacted with Hoechst 33342 (×1,000) at room temperature for 15 minutes and sealed with Fluoromount™. For the primary antibodies, a mouse anti-NeuN monoclonal antibody (×1000), a rabbit anti-Iba1 polyclonal antibody (×1,000), and a mouse anti-GFAP monoclonal antibody (×1,000) were diluted with a Can Get Signal immunostain solution A to be used. For the secondary antibodies, an Alexa 488 binding donkey anti-goat IgG antibody (×1,000), an Alexa 546 binding donkey anti-rabbit IgG antibody (×1,000), an Alexa 488 binding rabbit anti-mouse IgG antibody (×1,000), and an Alexa 546 binding rabbit anti-goat antibody (×1,000) were used. In addition, a control obtained by removing a primary antibodies was prepared for a negative control, and specificity of the primary antibodies was studied. The cut pieces were observed under a fluorescence microscope (BX50, Olympus Corporation) or a confocal laser microscope (FV10i, Olympus Corporation).

(9) Human Serum Sample

The examination was carried out after deliberation and approval by the ethical committee in Gifu University in accordance with the declaration of Helsinki. Furthermore, informed consents were executed to all subjects and name seals to consent forms for participation to the experiment were obtained. The subjects were 10 examples of sporadic ALS patients and 10 examples of the control group. All examinations using human serum samples were carried out in the School of Medicine, Gifu University. Ages, sexes, and timing for obtaining serums are shown in FIG. 8. The serum samples were preserved at −80° C. until the examination was carried out.

(10) ELISA Analysis

Quantification of GPNMB amounts in serums was carried out using Human Osteoactivin/GPNMB DuoSet in accordance with its protocol. A 96-well plate was coated with an anti-GPNMB antibody and blocking was carried out with a reagent diluent. The serum samples were taken out at −80° C. and unfrozen on ice. 96 µL of a reagent diluent was added to each well and a sample and a control were added in an each amount of 4 µL to be 25-fold diluted. The standard was also added after diluting in stages using a reagent diluent in the same manner. Then, the samples were incubated at room temperature for 2 hours. Each well was washed with a washing buffer and 100 µL of an anti-GPNMB detection antibody was added and incubated at room temperature for 2 hours. After washing each well, thereto was added 100 µL of streptavidin-HRP and incubated for 20 minutes under shielding light, and each well was then washed. 100 µL of a substrate solution was added and incubated for 20 minutes under shielding light, 50 µL of a reaction termination liquid was added, and then an absorbance at 450 nm was measured.

(11) Statistical Analysis

The experiment result was expressed by a mean value±standard error or a standard deviation. Statistical comparison was carried out by a Student's t-test using STAT VIEW (SAS institute, Curry, USA). Less than 5% of a risk rate was assumed to have a significant difference.

2. Results (1) ALS Gene Expression Profiling

Gene expression amounts in the spinal cords of SOD1$^{G93A}$ and wild-type (WT) mice were analyzed by a scatchard plot method (FIG. 1). When a gene group having twice or more expression and significant change in expressions between SOD1$^{G93A}$ mice and WT mice was analyzed by scatchard plot, expression of a gene group related to an immunologic response, an inflammatory reaction and a stress response was increased in the SOD1$^{G93A}$ mice as compared to the WT mice (FIG. 2). In particular, a transmembrane glycoprotein nmb (Glycoprotein (transmembrane) nmb; GPNMB) had the highest expression increase rate among ALS pathologic conditions. The following study was made by focusing on GPNMB based on these results.

(2) Real Time RT-PCR

Figure 3:
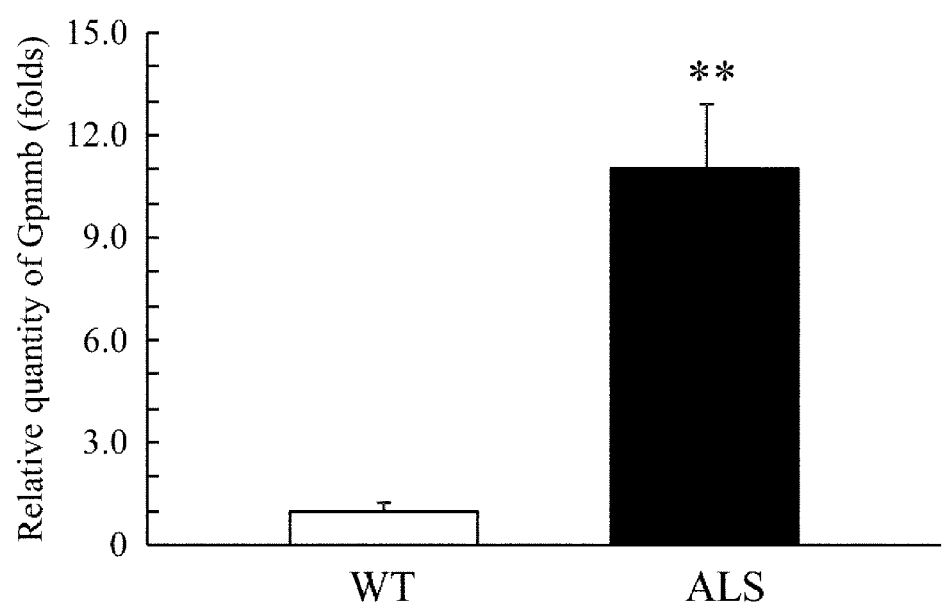
FIG. 3 is a graph showing mRNA amounts of GPNMB in the spinal cords of 14-week old SOD1$^{G93A}$ and WT mice. The data are expressed as means±standard error. ** P<0.01 vs. WT (Student's t-test).

GPNMB mRNA amounts in the spinal cords of 14-week old SOD1$^{G93A}$ and WT mice were measured using a real time PCR method. GPNMB mRNA was increased in the SOD1$^{G93A}$ mice to about 11 times as large as that of the WT mice (FIG. 3).

(3) Localization of GPNMB in Spinal Cord of Mouse

Figure 4:
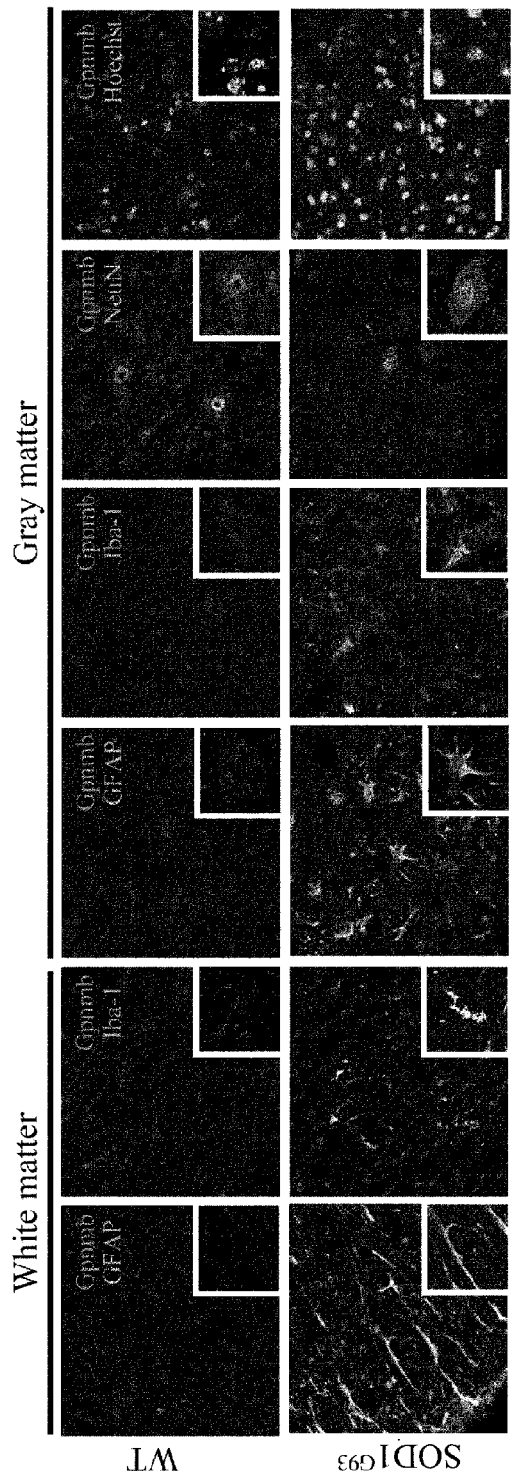
FIG. 4 is a view showing localization of GPNMB in the spinal cords of 14-week old SOD1$^{G93A}$ and WT mice. NeuN denotes a nerve cell, GFAP denotes an activated astrocyte, Iba-1 denotes microglia, and Hoechst denotes a nucleus, respectively. The scale bar indicates 50 μm.

In order to clarify localization of GPNMB in spinal cords of mice, NeuN, GFAP and Iba-1 immunofluorescence double staining was carried out. In the spinal cord gray matter of a 14-week old SOD1$^{G93A}$ mouse, an intensive expression of GPNMB was observed in a NeuN positive nerve cell and a GFAP positive activated astrocyte, but was not observed in an Iba-1 positive microglia and a nucleus (FIG. 4). In the same manner, in the spinal cord white matter, an intensive expression of GPNMB was observed in a GFAP positive activated astrocyte, but was not observed in an Iba-1 positive microglia (FIG. 4). These results suggest involvement of GPNMB in the formation of ALS pathologic conditions.

(4) Change in Expression of GPNMB Over Time in Spinal Cord of Mouse

Figure 5:
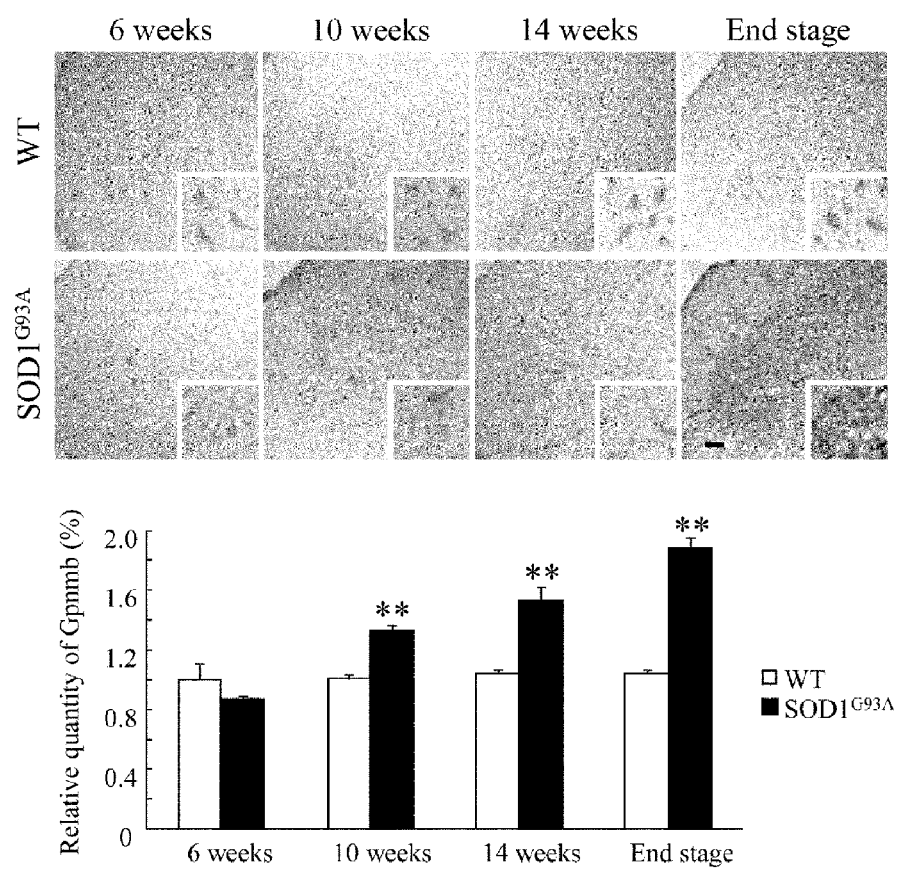
FIG. 5 shows a view showing change of GPNMB expression due to development of the ALS pathologic condition. The view shows GPNMB expressions in the spinal cords of SOD1$^{G93A}$ and WT mice in 6, 10, 14-week old and the terminal stage of the pathologic condition. The scale bar indicates 100 μm. The data are expressed as means±standard error. ** P<0.01 vs. WT (Student's t-test).

A SOD1$^{G93A}$ mouse had significant ($p<0.01$) increase of expression of GPNMB in the spinal cord from 10-week old as compared to a WT mouse, and the expression amount was increased accompanying development of the pathologic conditions (FIG. 5). On the other hand, change in an expression amount of GPNMB was not observed in a WT mouse (FIG. 5). These results suggest that GPNMB is a promising marker that reflects the ALS pathologic conditions. Furthermore, the fact that increase of GPNMB expression was observed before the onset strongly suggests that GPNMB could be a marker for earlier diagnosis for ALS.

(5) Expression of GPNMB in Human Spinal Cord

Figure 7:
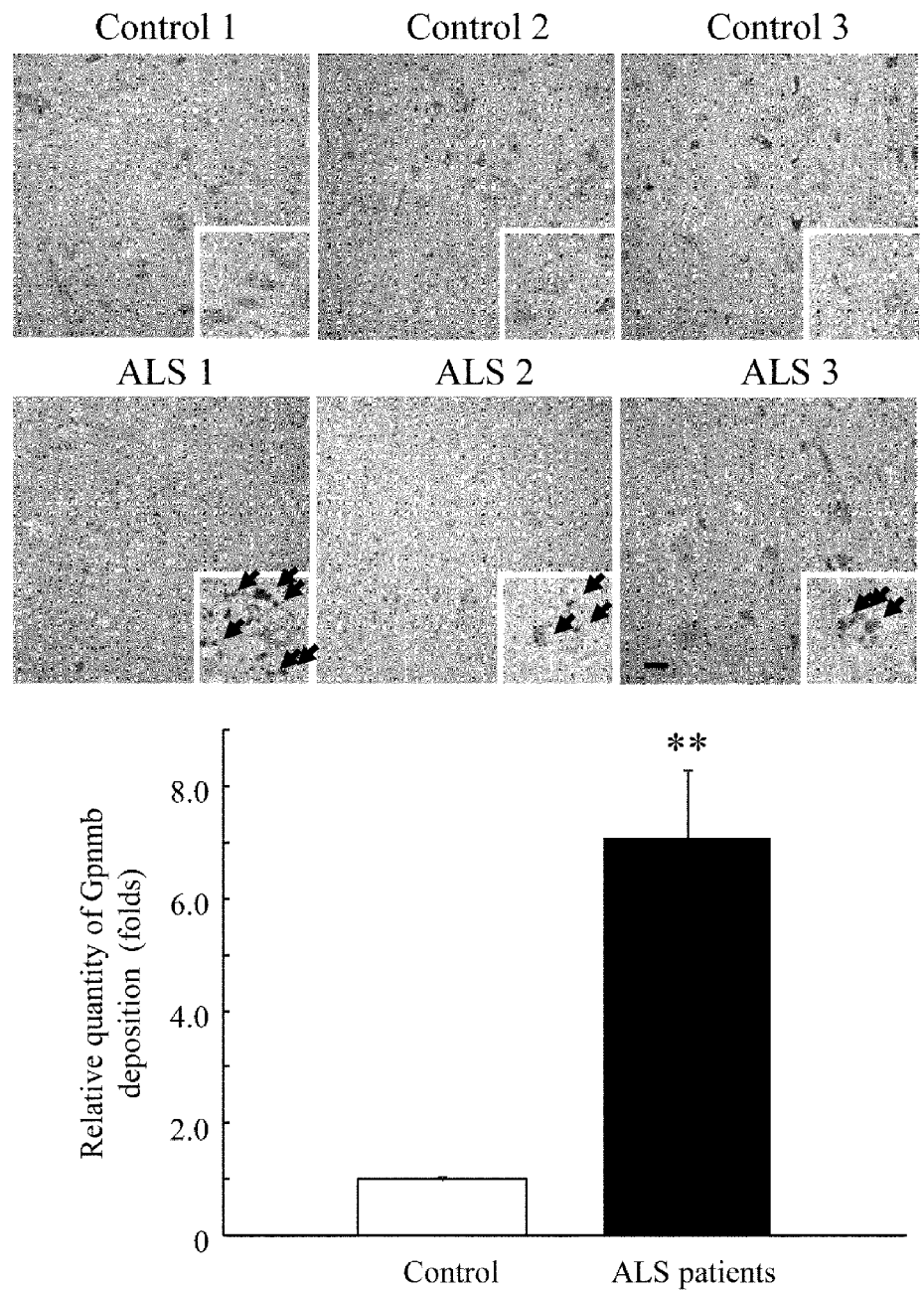
FIG. 7 is a view showing expression of GPNMB in the spinal cords of sporadic ALS and control disease patients. An arrow shows a GPNMB positive inclusion body in the spinal cord of a sporadic ALS patient. The scale bar indicates 100 μm. The data are expressed as means±standard error. ** P<0.01 vs. control group (Student's t-test).

In order to clarify involvement of GPNMB in the human ALS pathologic conditions, expression of GPNMB in the human spinal cord was studied using immunostaining. Backgrounds of patients are shown in FIG. 6. The total number of sporadic ALS patients was 3 (2 males, 1 female), and that of control disease patients was 3 (1 male, 2 females). Control diseases include brain stem infarction, polymyositis and multiple cerebral infarction. Ages of death of sporadic ALS and control disease patients were 62.0±16.1 years old and 68.0±3.5 years old, respectively. Post mortem intervals of sporadic ALS and control disease patients were 2.6±0.1 hours and 2.6±1.1 hours, respectively. A GPNMB positive aggregate was observed in the human spinal cord of a sporadic ALS patient, and the aggregate was significantly increased ($p<0.01$) in the spinal cord of a sporadic ALS patient as compared to the spinal cord of a control disease patient (FIG. 7). These results suggest that GPNMB is deeply involved in the formation of ALS pathologic conditions and that GPNMB is useful as a marker for ALS.

(6) GPNMB Concentration in Serum of Sporadic ALS Patient

Figure 9:
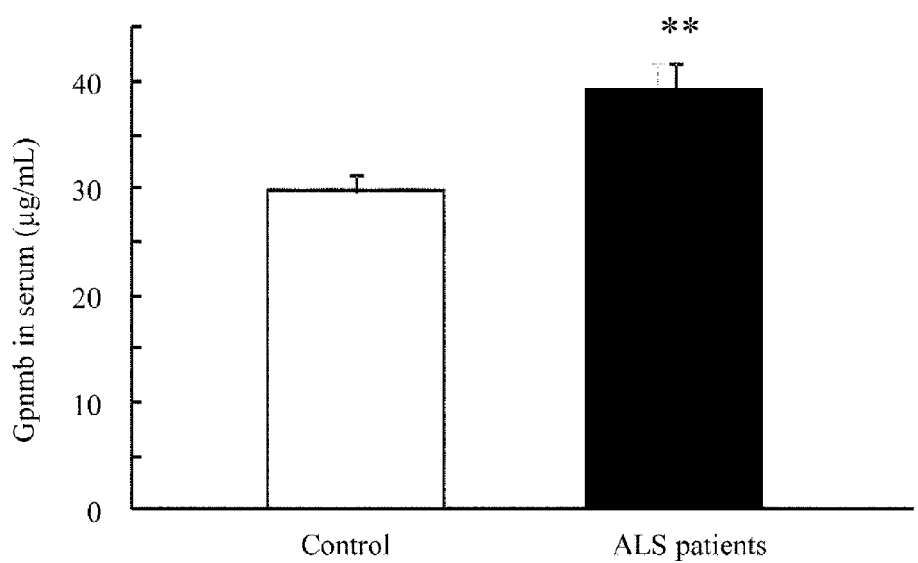
FIG. 9 is a view showing GPNMB concentrations in the serum in a sporadic ALS patient and a normal subject. The data are expressed with means±standard error. ** P<0.01 vs. control group (Student's t-test).

GPNMB concentrations in serums of sporadic ALS patients and normal subjects were measured by ELISA. Backgrounds of patients are shown in FIG. 8. The total number of sporadic ALS patients was 10 (7 males, 3 females), and that of normal subjects was 10 (3 males, 7 females). The ages of the sporadic ALS patients and the normal subjects were 66.4±10.1 years old and 45.5±20.7 years old, respectively. GPNMB concentrations in serums showed significantly high values ($p<0.01$) in the sporadic ALS patients (39.1±2.8 µg/mL) as compared to the normal subjects (average±standard error, 29.8±1.6 µg/mL) (FIG. 9). Thus, GPNMB was showed to be useful as a marker for ALS in a clinical use. The fact that the variation in the serums was able to be detected is extremely important for clinical application of GPNMB.

INDUSTRIAL APPLICABILITY

The detection method of the present invention enables to simply and objectively determine the possibility of the onset of ALS. The detection method of the present invention is useful as a means for determining whether ALS is developed or not. In addition, the detection method is also expected to be utilized as a means for figuring out the future possibility of the onset. Due to early discovery and early treatment utilizing the detection method of the present invention, it is expected to attempt prevention of intractability, severity (unfavorable progress), recurrence of ALS, and the like. Furthermore, the detection of the present invention is also expected to be utilized as a means for presuming prognosis.

The invention is not construed by description of the embodiments and examples of the invention described above at all. Various modified embodiments are also included in the invention within the range that a person skilled in the art can easily conceive of, without deviating from the description of the scope of patent claims.

Contents of treatises, unexamined patent publications, and examined patent publications specified in this specification are all incorporated herein by reference.

The invention claimed is:

1. A method for detecting amyotrophic lateral sclerosis (ALS), the method comprising:
obtaining a specimen from a subject suspected of having ALS or at high risk of having ALS, wherein the specimen is blood, plasma, serum, spinal cord, or cerebrospinal fluid;
detecting the level of expression of a transmembrane glycoprotein nmb in the subject specimen, wherein the transmembrane glycoprotein consists of the amino acid sequence of SEQ ID NO:1 or SEQ ID NO:3; and
comparing the level of expression in the specimen with a control specimen, wherein a significant increase in level of expression in the subject specimen compared to the control specimen indicates the present or future possibility of the onset of amyotrophic lateral sclerosis.

2. The method for detecting amyotrophic lateral sclerosis according to claim 1 wherein the control specimen is a subject specimen obtained from the same subject at an earlier time.

3. The method of claim 1, wherein the detecting step comprises detecting the level of expression of a transmembrane glycoprotein nmb in the subject specimen with a substance having a specific binding activity to a marker for amyotrophic lateral sclerosis consisting of the amino acid sequence of SEQ ID NO:1 or SEQ ID NO:3.

4. The method of claim 3, wherein the substance is an antibody.

5. A method for early stage detection of amyotrophic lateral sclerosis in a subject, the method comprising:
obtaining a specimen from a subject suspected of having ALS or at high risk of having ALS, wherein the specimen is a spinal cord or serum specimen;
detecting the level of expression of a transmembrane glycoprotein nmb in the subject specimen, wherein the transmembrane glycoprotein consists of the amino acid sequence of SEQ ID NO:1 or SEQ ID NO:3; and
comparing the level of expression in the specimen with a control specimen, wherein a significant increase in level of expression in the subject specimen compared to the control specimen indicates the presence of amyotrophic lateral sclerosis at an early stage.

6. The method of claim 2 or claim 5, wherein the amino acid sequence of SEQ ID NO: 1 is encoded by the nucleic acid sequence of SEQ ID NO: 2.

7. The method of claim 2 or claim 5, wherein the amino acid sequence of SEQ ID NO: 3 is encoded by the nucleic acid sequence of SEQ ID NO: 4.

* * * * *

SEQUENCE LISTING

```
<160> NUMBER OF SEQ ID NOS: 8

<210> SEQ ID NO 1
<211> LENGTH: 572
<212> TYPE: PRT
<213> ORGANISM: Homo sapiens

<400> SEQUENCE: 1

Met Glu Cys Leu Tyr Tyr Phe Leu Gly Phe Leu Leu Leu Ala Ala Arg
1               5                  10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
    50                  55                  60

Gly Asp Met Arg Trp Lys Asn Ser Trp Lys Gly Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
    130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
    210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
                260                 265                 270
```

```
Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
        290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Arg Pro Ser Lys Pro Thr
                325                 330                 335

Pro Ser Leu Ala Thr Thr Leu Lys Ser Tyr Asp Ser Asn Thr Pro Gly
            340                 345                 350

Pro Ala Gly Asp Asn Pro Leu Glu Leu Ser Arg Ile Pro Asp Glu Asn
            355                 360                 365

Cys Gln Ile Asn Arg Tyr Gly His Phe Gln Ala Thr Ile Thr Ile Val
        370                 375                 380

Glu Gly Ile Leu Glu Val Asn Ile Ile Gln Met Thr Asp Val Leu Met
385                 390                 395                 400

Pro Val Pro Trp Pro Glu Ser Ser Leu Ile Asp Phe Val Val Thr Cys
                405                 410                 415

Gln Gly Ser Ile Pro Thr Glu Val Cys Thr Ile Ile Ser Asp Pro Thr
            420                 425                 430

Cys Glu Ile Thr Gln Asn Thr Val Cys Ser Pro Val Asp Val Asp Glu
        435                 440                 445

Met Cys Leu Leu Thr Val Arg Arg Thr Phe Asn Gly Ser Gly Thr Tyr
450                 455                 460

Cys Val Asn Leu Thr Leu Gly Asp Asp Thr Ser Leu Ala Leu Thr Ser
465                 470                 475                 480

Thr Leu Ile Ser Val Pro Asp Arg Asp Pro Ala Ser Pro Leu Arg Met
                485                 490                 495

Ala Asn Ser Ala Leu Ile Ser Val Gly Cys Leu Ala Ile Phe Val Thr
            500                 505                 510

Val Ile Ser Leu Leu Val Tyr Lys Lys His Lys Glu Tyr Asn Pro Ile
        515                 520                 525

Glu Asn Ser Pro Gly Asn Val Val Arg Ser Lys Gly Leu Ser Val Phe
        530                 535                 540

Leu Asn Arg Ala Lys Ala Val Phe Phe Pro Gly Asn Gln Glu Lys Asp
545                 550                 555                 560

Pro Leu Leu Lys Asn Gln Glu Phe Lys Gly Val Ser
            565                 570

<210> SEQ ID NO 2
<211> LENGTH: 2775
<212> TYPE: DNA
<213> ORGANISM: Homo sapiens

<400> SEQUENCE: 2
tgccgcttaa taccatcaca tgatcctccc cgaggccctg tatttaatta aaatagagag    60
ggaggcacca cagatgccag aagaacactg ttgctcttgg tggacgggcc cagaggaatt   120
cagagttaaa ccttgagtgc ctgcgtccgt gagaattcag catggaatgt ctctactatt   180
tcctgggatt tctgctcctg gctgcaagat tgccacttga tgccgccaaa cgatttcatg   240
atgtgctggg caatgaaaga ccttctgctt acatgaggga gcacaatcaa ttaaatggct   300
ggtcttctga tgaaaatgac tggaatgaaa aactctaccc agtgtggaag cggggagaca   360
tgaggtggaa aaactcctgg aagggaggcc gtgtgcaggc ggtcctgacc agtgactcac   420
```

```
cagccctcgt gggctcaaat ataacatttg cggtgaacct gatattccct agatgccaaa      480
aggaagatgc caatggcaac atagtctatg agaagaactg cagaaatgag ctggtttat       540 ctgctgatcc gtatgtttac aactggacag catggtcaga ggacagtgac ggggaaaatg     600
gcaccggcca aagccatcat aacgtcttcc ctgatgggaa acctttcct caccaccccg       660 gatggagaag atggaatttc atctacgtct tccacacact tggtcagtat ttcagaaat       720 tgggacgatg ttcagtgaga gtttctgtga acacagccaa tgtgacactt gggcctcaac     780
tcatggaagt gactgtctac agaagacatg gacgggcata tgttcccatc gcacaagtga     840
aagatgtgta cgtggtaaca gatcagattc ctgtgtttgt gactatgttc cagaagaacg     900
atcgaaattc atccgacgaa accttcctca agatctccc cattatgttt gatgtcctga       960
ttcatgatcc tagccacttc ctcaattatt ctaccattaa ctacaagtgg agcttcgggg     1020
ataatactgg cctgtttgtt ccaccaatc atactgtgaa tcacacgtat gtgctcaatg      1080
gaaccttcag cctaacctc actgtgaaag ctgcagcacc aggaccttgt ccgccaccgc      1140
caccaccacc cagaccttca aaacccaccc cttctttagc aactactcta aaatcttatg    1200
attcaaacac cccaggacct gctggtgaca acccctgga gctgagtagg attcctgatg     1260
aaaactgcca gattaacaga tatggccact ttcaagccac catcacaatt gtagagggaa    1320
tcttagaggt taacatcatc cagatgacag acgtcctgat gccggtgcca tggcctgaaa    1380
gctccctaat agactttgtc gtgacctgcc aagggagcat tcccacggag gtctgtacca   1440
tcatttctga ccccacctgc gagatcaccc agaacacagt ctgcagccct gtggatgtgg   1500
atgagatgtg tctgctgact gtgagacgaa ccttcaatgg gtctgggacg tactgtgtga    1560
acctcaccct gggggatgac acaagcctgg ctctcacgag cacccctgatt tctgttcctg   1620 acagagaccc agcctcgcct taaggatgg caaacagtgc cctgatctcc gttggctgct   1680
tggccatatt tgtcactgtg atctccctct tggtgtacaa aaaacacaag gaatacaacc   1740
caatagaaaa tagtcctggg aatgtggtca gaagcaaagg cctgagtgtc tttctcaacc    1800
gtgcaaaagc cgtgttcttc ccgggaaacc aggaaaagga tccgctactc aaaaaccaag    1860
aatttaaagg agtttcttaa atttcgacct tgtttctgaa gctcactttt cagtgccatt    1920
gatgtgagat gtgctggagt ggctattaac cttttttttcc taaagattat tgttaaatag   1980
atattgtggt ttggggaagt tgaatttttt ataggttaaa tgtcatttta gagatgggga    2040
gagggattat actgcaggca gcttcagcca tgttgtgaaa ctgataaaag caacttagca    2100
aggcttcttt tcattattt ttatgtttca cttataaagt cttaggtaac tagtaggata      2160
gaaacactgt gtcccgagag taaggagaga agctactatt gattagagcc taacccaggt   2220
taactgcaag aagaggcggg atactttcag cttttccatgt aactgtatgc ataaagccaa    2280
tgtagtccag tttctaagat catgttccaa gctaactgaa tcccacttca atacacactc   2340
atgaactcct gatggaacaa taacaggccc aagcctgtgg tatgatgtgc acacttgcta   2400
gactcagaaa aaatactact ctcataaatg ggtgggagta ttttggtgac aacctacttt    2460
gcttggctga gtgaaggaat gatattcata tattcattta ttccatggac atttagttag    2520 tgcttttat ataccaggca tgatgctgag tgacactctt gtgtatattt ccaaattttt     2580
gtacagtcgc tgcacatatt tgaaatcata tattaagact ttccaaagat gaggtccctg    2640 gttttttcatg gcaacttgat cagtaaggat ttcacctctg tttgtaacta aaaccatcta    2700
ctatatgtta gacatgacat tctttttctc tccttcctga aaaataaagt gtgggaagag   2760
acaagaaaaa aaaaa                                                      2775
```

<210> SEQ ID NO 3
<211> LENGTH: 560
<212> TYPE: PRT
<213> ORGANISM: Homo sapiens

<400> SEQUENCE: 3

Met Glu Cys Leu Tyr Tyr Phe Leu Gly Phe Leu Leu Leu Ala Ala Arg
1               5                   10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
50                  55                  60

Gly Asp Met Arg Trp Lys Asn Ser Trp Lys Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Ser Asp Gly
130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
210                 215                 220

Gln Val Lys Asp Val Tyr Val Thr Asp Gln Ile Pro Val Phe Val
225                 230                 235                 240

Thr Met Phe Gln Lys Asn Asp Arg Asn Ser Asp Glu Thr Phe Leu
                245                 250                 255

Lys Asp Leu Pro Ile Met Phe Asp Val Leu Ile His Pro Ser His
            260                 265                 270

Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
290                 295                 300

Leu Asn Gly Thr Phe Ser Leu Asn Leu Thr Val Lys Ala Ala Pro
305                 310                 315                 320

Gly Pro Cys Pro Pro Pro Pro Pro Arg Pro Ser Lys Pro Thr
                325                 330                 335

Pro Ser Leu Gly Pro Ala Gly Asp Asn Pro Leu Glu Leu Ser Arg Ile
            340                 345                 350

Pro Asp Glu Asn Cys Gln Ile Asn Arg Tyr Gly His Phe Gln Ala Thr
        355                 360                 365

Ile Thr Ile Val Glu Gly Ile Leu Glu Val Asn Ile Ile Gln Met Thr
370                 375                 380

-continued

Asp Val Leu Met Pro Val Pro Trp Pro Glu Ser Ser Leu Ile Asp Phe
385                 390                 395                 400

Val Val Thr Cys Gln Gly Ser Ile Pro Thr Glu Val Cys Thr Ile Ile
            405                 410                 415

Ser Asp Pro Thr Cys Glu Ile Thr Gln Asn Thr Val Cys Ser Pro Val
        420                 425                 430

Asp Val Asp Glu Met Cys Leu Leu Thr Val Arg Arg Thr Phe Asn Gly
    435                 440                 445

Ser Gly Thr Tyr Cys Val Asn Leu Thr Leu Gly Asp Asp Thr Ser Leu
450                 455                 460

Ala Leu Thr Ser Thr Leu Ile Ser Val Pro Asp Arg Asp Pro Ala Ser
465                 470                 475                 480

Pro Leu Arg Met Ala Asn Ser Ala Leu Ile Ser Val Gly Cys Leu Ala
                485                 490                 495

Ile Phe Val Thr Val Ile Ser Leu Leu Val Tyr Lys Lys His Lys Glu
            500                 505                 510

Tyr Asn Pro Ile Glu Asn Ser Pro Gly Asn Val Val Arg Ser Lys Gly
        515                 520                 525

Leu Ser Val Phe Leu Asn Arg Ala Lys Ala Val Phe Phe Pro Gly Asn
    530                 535                 540

Gln Glu Lys Asp Pro Leu Leu Lys Asn Gln Glu Phe Lys Gly Val Ser
545                 550                 555                 560

<210> SEQ ID NO 4
<211> LENGTH: 2739
<212> TYPE: DNA
<213> ORGANISM: Homo sapiens

<400> SEQUENCE: 4
tgccgcttaa taccatcaca tgatcctccc cgaggccctg tatttaatta aaatagagag      60
ggaggcacca cagatgccag aagaacactg ttgctcttgg tggacgggcc cagaggaatt     120
cagagttaaa ccttgagtgc ctgcgtccgt gagaattcag catggaatgt ctctactatt     180
tcctgggatt tctgctcctg gctgcaagat tgccacttga tgccgccaaa cgatttcatg     240
atgtgctggg caatgaaaga ccttctgctt acatgaggga gcacaatcaa ttaaatggct     300
ggtcttctga tgaaaatgac tggaatgaaa aactctaccc agtgtggaag cggggagaca     360
tgaggtggaa aaactcctgg aagggaggcc gtgtgcaggc ggtcctgacc agtgactcac     420
cagccctcgt gggctcaaat ataacatttg cggtgaacct gatattccct agatgccaaa     480
aggaagatgc caatggcaac atagtctatg agaagaactg cagaaatgag ctggtttat      540 ctgctgatcc gtatgtttac aactggacag catggtcaga ggacagtgac ggggaaaatg     600
gcaccggcca aagccatcat aacgtcttcc ctgatgggaa cctttttcct caccaccccg     660
gatggagaag atggaatttc atctacgtct ccacacact tggtcagtat ttccagaaat      720
tgggacgatg ttcagtgaga gtttctgtga acacagccaa tgtgacactt gggcctcaac     780
tcatggaagt gactgtctac agaagacatg gacgggcata tgttcccatc gcacaagtga     840 agatgtgta cgtggtaaca gatcagattc tgtgtttgt gactatgttc cagaagaacg      900
atcgaaattc atccgacgaa accttcctca agatctccc cattatgttt gatgtcctga     960
ttcatgatcc tagccacttc ctcaattatt ctaccattaa ctacaagtgg agcttcgggg    1020 ataaatactgg cctgtttgtt tccaccaatc atactgtgaa tcacacgtat gtgctcaatg    1080
gaaccttcag ccttaacctc actgtgaaag ctgcagcacc aggaccttgt ccgccaccgc    1140
caccaccacc cagaccttca aaacccaccc cttctttagg acctgctggt gacaaccccc    1200

-continued

```
tggagctgag taggattcct gatgaaaact gccagattaa cagatatggc cactttcaag    1260
ccaccatcac aattgtagag ggaatcttag aggttaacat catccagatg acagacgtcc    1320
tgatgccggt gccatggcct gaaagctccc taatagactt tgtcgtgacc tgccaaggga    1380
gcattcccac ggaggtctgt accatcattt ctgacccac ctgcgagatc acccagaaca    1440
cagtctgcag ccctgtggat gtggatgaga tgtgtctgct gactgtgaga cgaaccttca    1500
atgggtctgg gacgtactgt gtgaacctca ccctggggga tgacacaagc ctggctctca    1560
cgagcaccct gatttctgtt cctgacagag acccagcctc gcctttaagg atggcaaaca    1620
gtgccctgat ctccgttggc tgcttggcca tatttgtcac tgtgatctcc ctcttggtgt    1680
acaaaaaaca caaggaatac aacccaatag aaaatagtcc tgggaatgtg gtcagaagca    1740
aaggcctgag tgtctttctc aaccgtgcaa agccgtgtt cttcccggga aaccaggaaa    1800
aggatccgct actcaaaaac caagaattta aaggagtttc ttaaatttcg accttgtttc    1860
tgaagctcac ttttcagtgc cattgatgtg agatgtgctg gagtggctat taacctttt    1920 ttcctaaaga ttattgttaa atagatattg tggtttgggg aagttgaatt ttttataggt    1980
taaatgtcat tttagagatg gggagaggga ttatactgca ggcagcttca gccatgttgt    2040
gaaactgata aaagcaactt agcaaggctt cttttcatta tttttatgt ttcacttata    2100 aagtcttagg taactagtag gatagaaaca ctgtgtcccg agagtaagga gagaagctac    2160
tattgattag agcctaaccc aggttaactg caagaagagg cgggatactt tcagcttttcc    2220 atgtaactgt atgcataaag ccaatgtagt ccagtttcta agatcatgtt ccaagctaac    2280
tgaatcccac ttcaatacac actcatgaac tcctgatgga acaataacag gcccaagcct    2340
gtggtatgat gtgcacactt gctagactca gaaaaaatac tactctcata aatgggtggg    2400
agtattttgg tgacaaccta ctttgcttgg ctgagtgaag gaatgatatt catatattca    2460
tttattccat ggacatttag ttagtgcttt ttatatacca ggcatgatgc tgagtgacac    2520
tcttgtgtat atttccaaat ttttgtacag tcgctgcaca tatttgaaat catatattaa    2580
gactttccaa agatgaggtc cctggttttt catggcaact tgatcagtaa ggatttcacc    2640
tctgtttgta actaaaacca tctactatat gttagacatg acattcttt tctctccttc    2700 ctgaaaaata aagtgtggga agagacaaga aaaaaaaa                            2739
```

<210> SEQ ID NO 5
<211> LENGTH: 21
<212> TYPE: DNA
<213> ORGANISM: Artificial Sequence
<220> FEATURE:
<223> OTHER INFORMATION: sense primer

<400> SEQUENCE: 5
tctgaaccga gccctgacat c                                              21

<210> SEQ ID NO 6
<211> LENGTH: 21
<212> TYPE: DNA
<213> ORGANISM: Artificial Sequence
<220> FEATURE:
<223> OTHER INFORMATION: antisense primer

<400> SEQUENCE: 6
agcagtagcg gccatgtgaa g                                              21

<210> SEQ ID NO 7
<211> LENGTH: 20

```
<212> TYPE: DNA
<213> ORGANISM: Artificial Sequence
<220> FEATURE:
<223> OTHER INFORMATION: sense primer

<400> SEQUENCE: 7
tgtgtccgtc gtggatctga                                               20

<210> SEQ ID NO 8
<211> LENGTH: 21
<212> TYPE: DNA
<213> ORGANISM: Artificial Sequence
<220> FEATURE:
<223> OTHER INFORMATION: antisense primer

<400> SEQUENCE: 8
ttgctgttga agtcgcagga g                                             21
```